United States Patent
Malinin et al.

(10) Patent No.: US 7,335,381 B2
(45) Date of Patent: Feb. 26, 2008

(54) TRANSPLANTABLE PARTICULATE BONE COMPOSITION HAVING HIGH OSTEOINDUCTIVE CAPACITY AND METHODS FOR MAKING AND USING SAME

(75) Inventors: Theodore I. Malinin, Key Biscayne, FL (US); H. Thomas Temple, Miami, FL (US); Alvaro Flores, Hialeah, FL (US); Billy E. Buck, Miami, FL (US)

(73) Assignee: Losec, Inc, Houston, TX (US)

( * ) Notice: Subject to any disclaimer, the term of this patent is extended or adjusted under 35 U.S.C. 154(b) by 46 days.

(21) Appl. No.: 10/956,487

(22) Filed: Oct. 1, 2004

(65) Prior Publication Data

US 2005/0152987 A1    Jul. 14, 2005

Related U.S. Application Data

(60) Provisional application No. 60/508,191, filed on Oct. 2, 2003.

(51) Int. Cl.
*A61K 35/32*    (2006.01)
(52) U.S. Cl. ...................................... 424/549
(58) Field of Classification Search .......... 424/549, 424/422, 423

See application file for complete search history.

(56) References Cited

U.S. PATENT DOCUMENTS 6,340,477 B1 * 1/2002 Anderson .................. 424/488
6,692,532 B1 * 2/2004 Healy et al. .............. 623/23.51

OTHER PUBLICATIONS

Wu J-J et al. "Fine powdering exposes the mineral-protected collagen of bone to protease digestion". Calcified Tissue International, 1988, 42(4): 243-247. entire document.*
The terms "Autograft", "Allograft", and "Xenograft". see at the web http://www.m-w.com. pp. 1-4, Mar. 4, 2006.*

* cited by examiner

*Primary Examiner*—Sandra E. Saucier
*Assistant Examiner*—Satyendra K. Singh
(74) *Attorney, Agent, or Firm*—Robert W Strozier

(57) ABSTRACT

A particulate bone of defined sizes which has a unique property of direct bone osteoinduction without going through endochondral ossification stage is disclosed. The bone is not subjected to chemical extraction or decalcification. This allows for the retention of all physiologically active components of native bone. The invention hinges on the newly discovered ability of bone particles of defined sizes to exert osteoinduction by a pathway superior to and distinct from demineralized bone matrix and similar preparations.

37 Claims, 15 Drawing Sheets

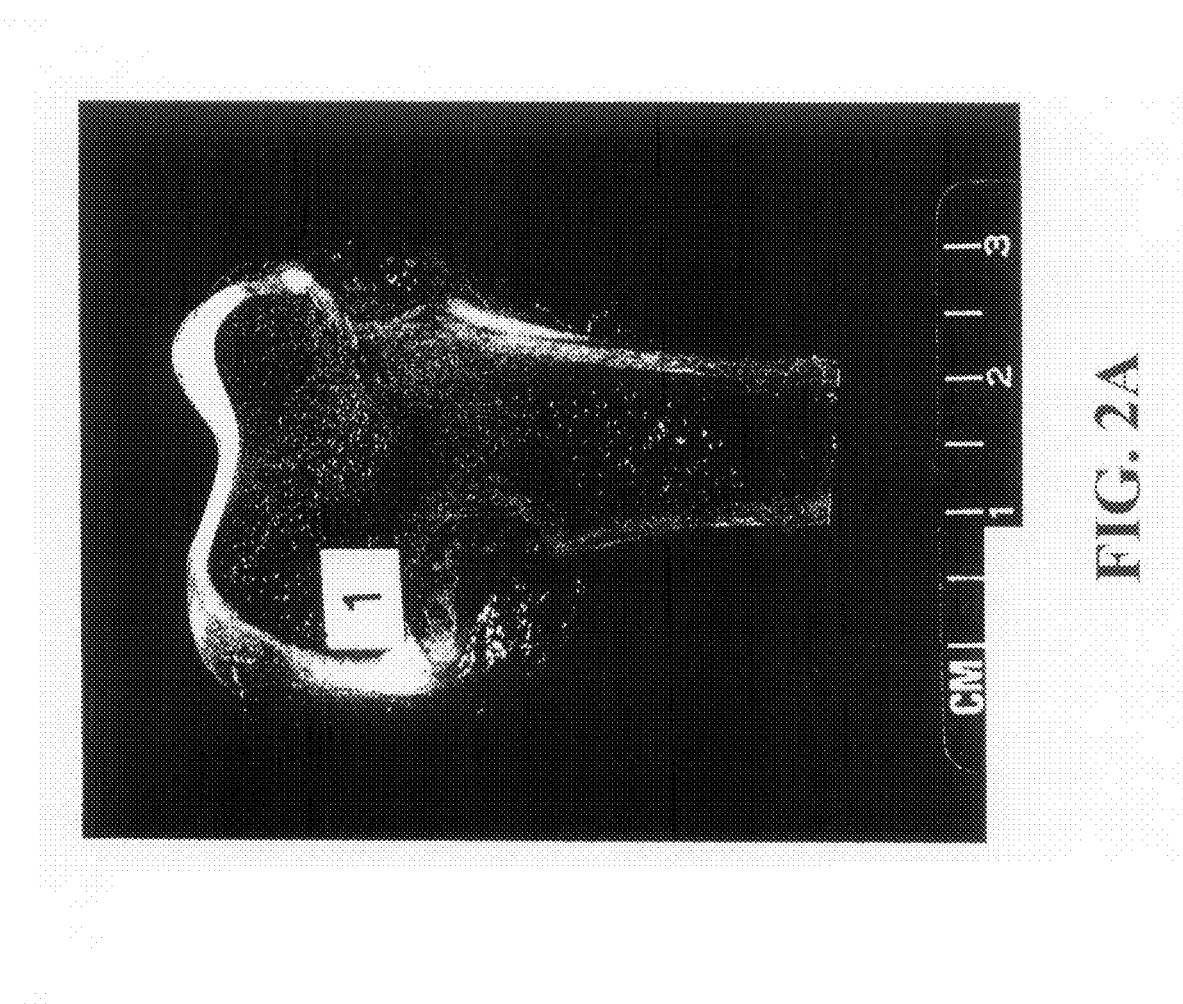

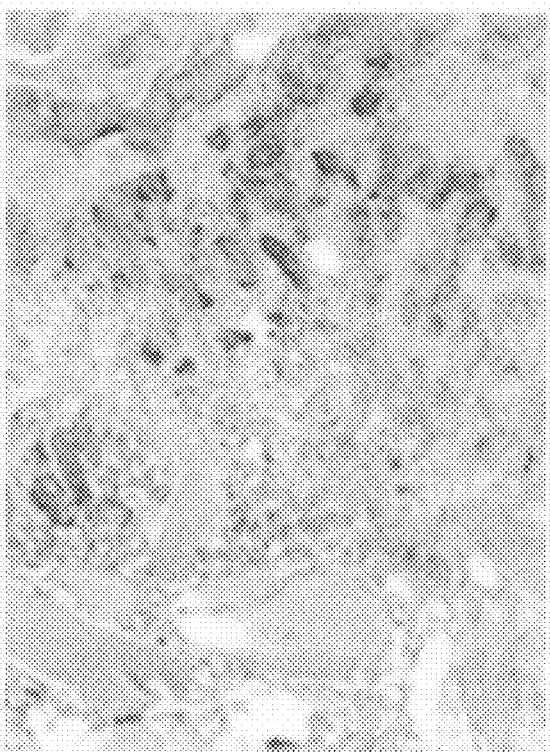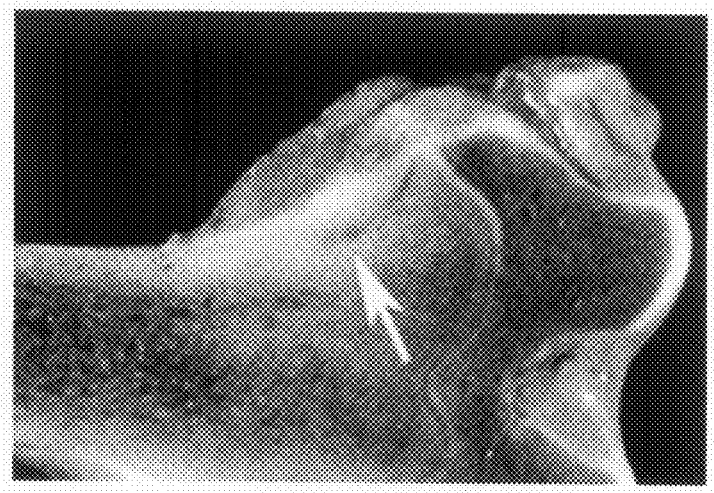

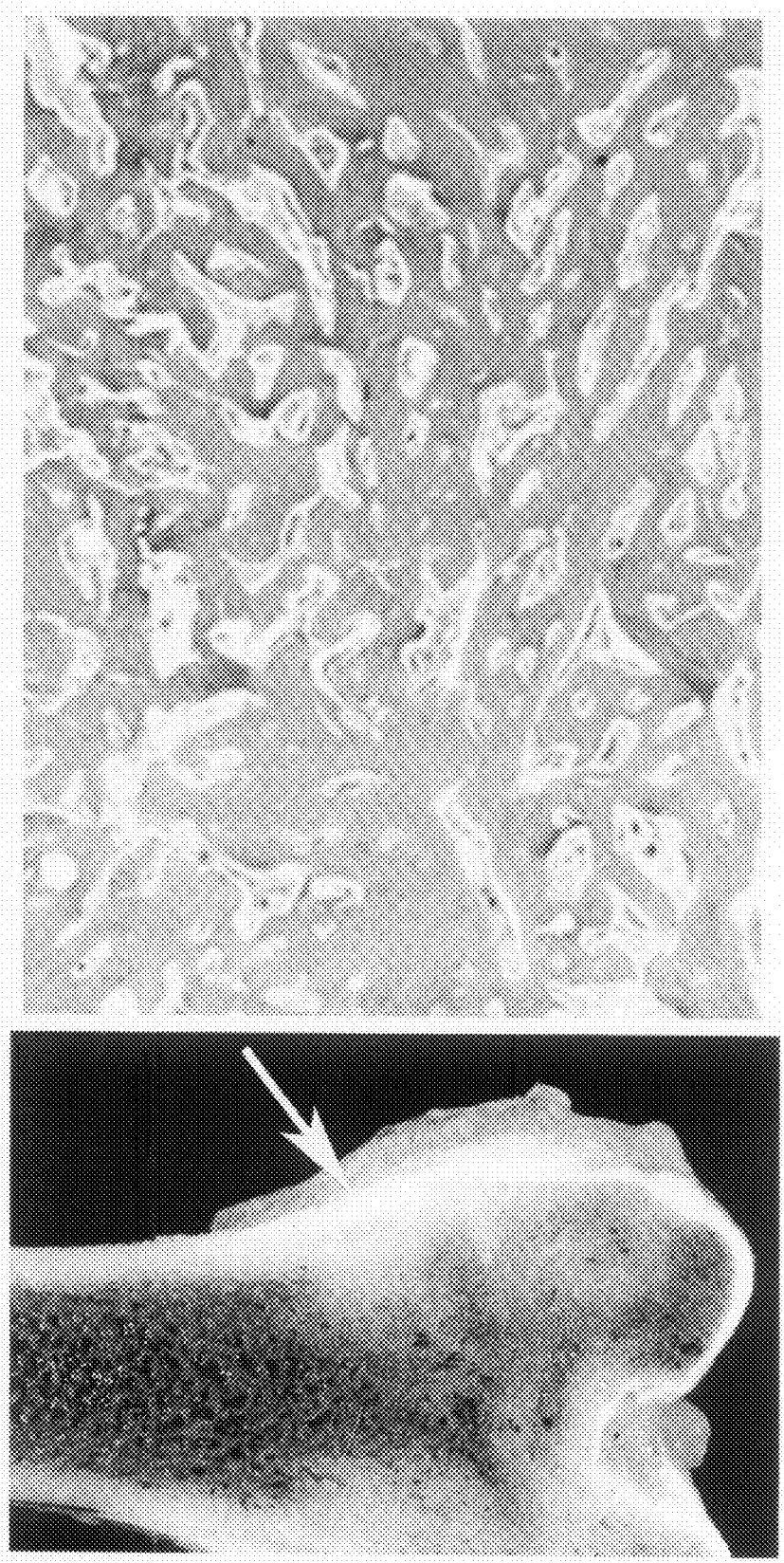

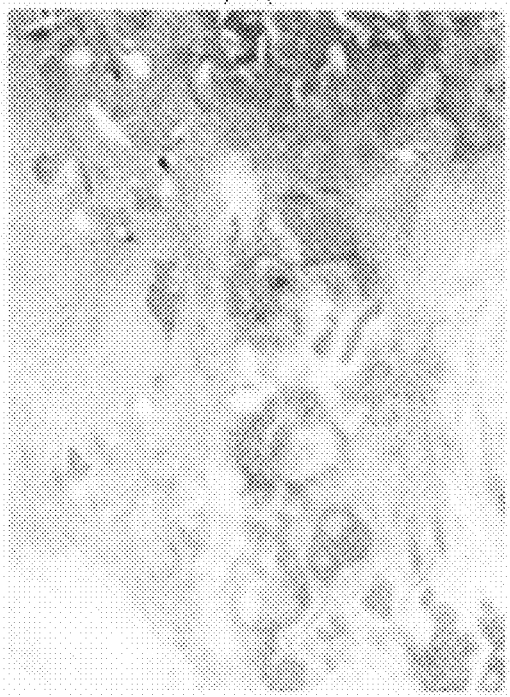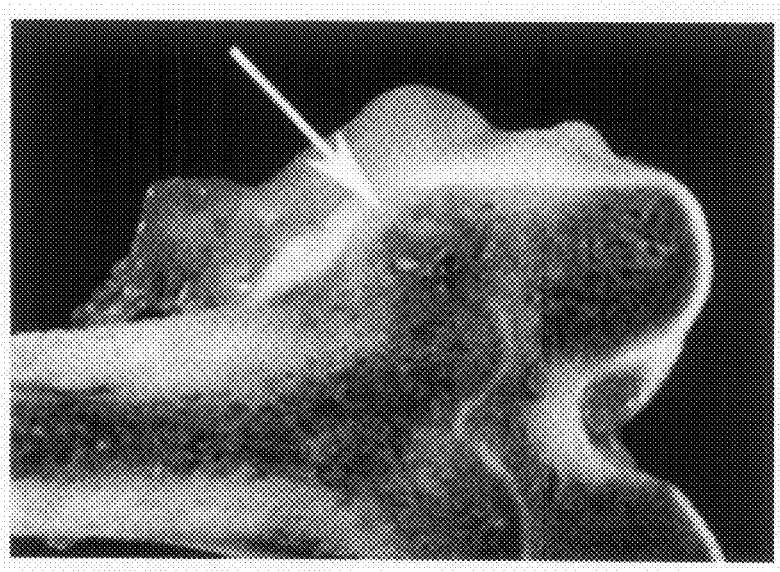

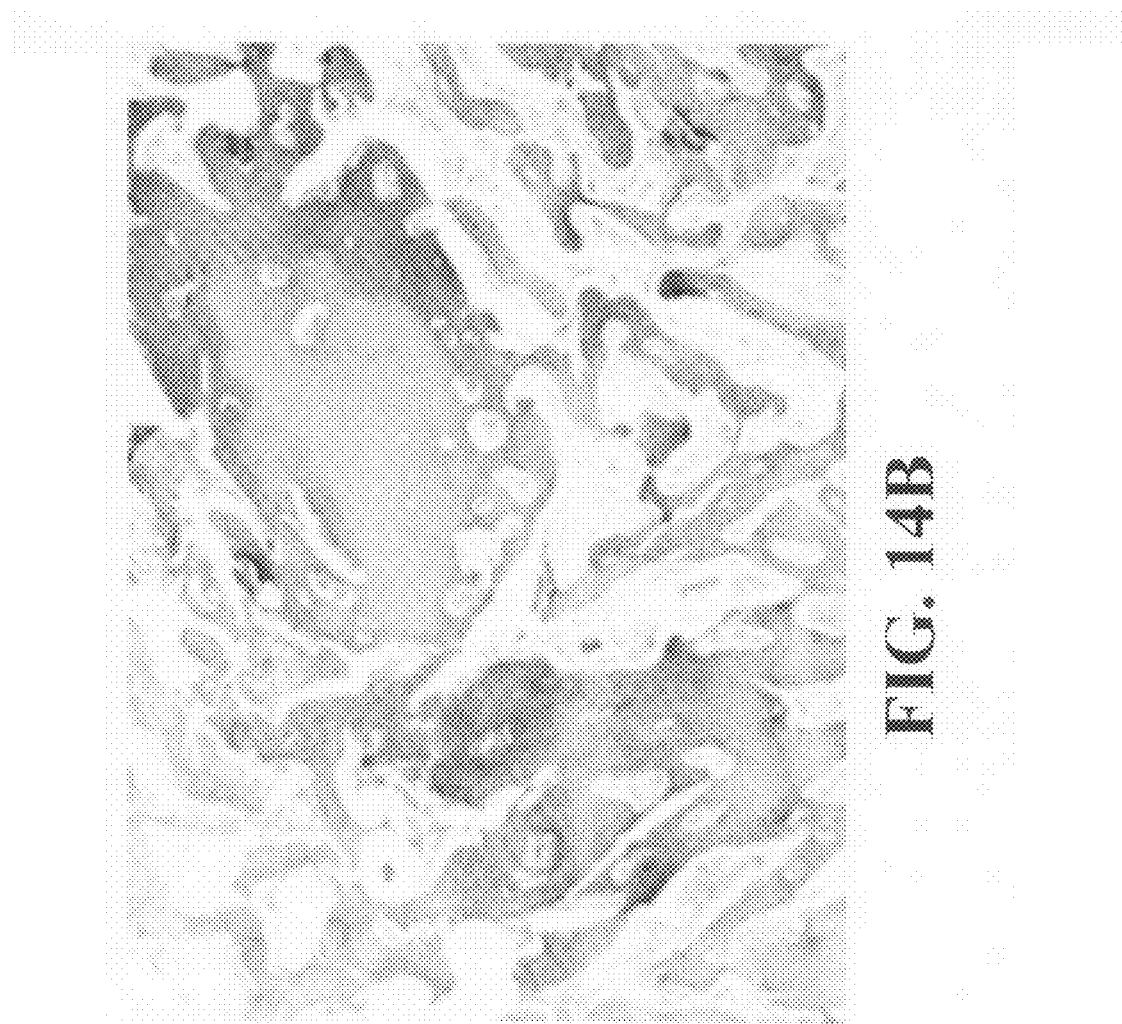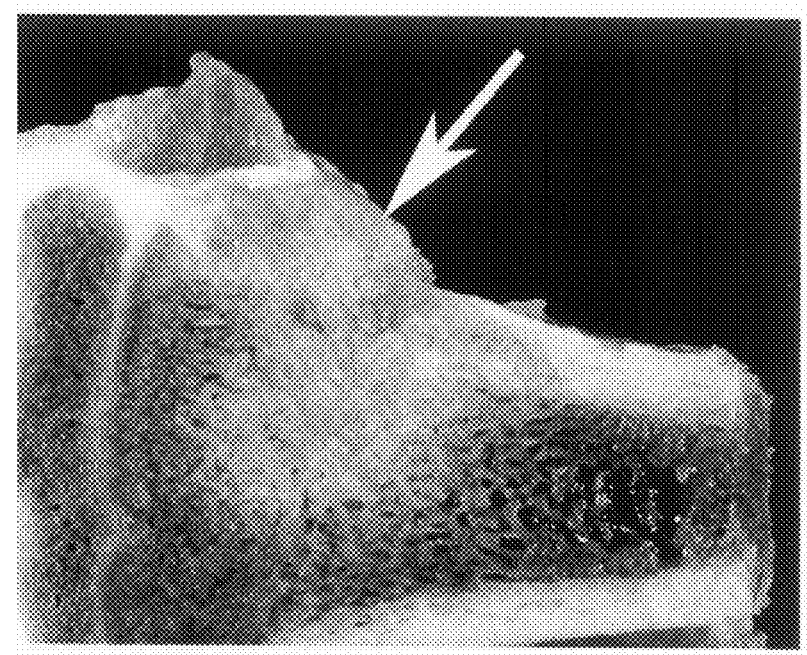

TRANSPLANTABLE PARTICULATE BONE COMPOSITION HAVING HIGH OSTEOINDUCTIVE CAPACITY AND METHODS FOR MAKING AND USING SAME

RELATED APPLICATIONS

This application claims provisional priority to U.S. Provisional Patent Application Ser. No. 60/508,191 filed 2 Oct. 2003.

BACKGROUND OF THE INVENTION

1. Field of the Invention

The present invention relates to a process and a method for producing osteoinductive particulate bone compositions or preparations, where the bone particles have improved osteoinduction activity and to methods for making and using same.

More particularly, the present invention relates to a process and a method for producing osteoinductive particulate bone compositions or preparations including a distribution of bone particles sizes, where the particles sizes are less that 355 μm or simply 355μ and where the bone particles have improved osteoinductive activity.

2. Description of the Related Art

It is well known that implantation of bone decalcified with hydrochloric acid or of demineralized bone matrix into musculature of rodents leads to heterotopic bone formation (Urist, et al. 1983 and others). In fact, this is a standard laboratory test devised by Urist for the detection of bone morphogenetic protein (BMP) activity in various bone preparations. However, rodent animal models have a limitation, as these animals are peculiar in their ability to produce heterotopic cancellous bone in response to implantation of several tissues including bone and various bone preparations. Whether this parallels response in higher animals or in humans is unknown. However, the rodent animal model is a convenient one and it is easy to use.

It has been shown as early as the 1950's (LaCroix) that exposure of bone (autologous or allogeneic) to alcohol or to heat markedly diminishes its osteoinductive capacity. It has been also established, but is not necessarily acknowledged that intraosseous lipids serve as vehicle for BMP. Extraction of the same from bone allografts would likely interfere with the delivery of BMP or other growth factors at the site of osteoinductivity.

Thus, there is a need in the art for a particulate bone preparation that has superior initial osteoinductive capacity than traditional demineralized or chemically extracted bone.

SUMMARY OF THE INVENTION

Compositions

The present invention provides a particulate bone composition with improved osteogenic capacity or osteoinductive activity.

The present invention also provides a particulate bone composition including a particle size distribution of nascent bone particles with improved osteogenic capacity or osteoinductive activity.

The present invention also provides a particulate bone composition including a particle size distribution of nascent bone particles, allograft bone particles or mixtures or combinations thereof with improved osteogenic capacity or osteoinductive activity.

The present invention also provides a particulate bone composition including a particle size distribution of nascent bone particles, allograft bone particles or mixtures or combinations thereof with improved osteogenic capacity or osteoinductive activity, where the particles have a particle size less than or equal to about 355μ, where μ means microns ($1 \times 10^{-6}$m).

The present invention also provides an undemineralized, freeze dried particulate bone composition including a particle size distribution of nascent bone particles, allograft bone particles or mixtures or combinations thereof with improved osteogenic capacity or osteoinductive activity, where the particles having particle sizes between about 25μ and about 355μ.

The present invention also provides a particulate bone composition including a particle size distribution of nascent bone particles, allograft bone particles or mixtures or combinations thereof with improved osteogenic capacity or osteoinductive activity, where the particles have a particle size less than or equal to about 355μ and having a distribution of particles having particles sizes between 355μ and 250μ, between 250μ, and 150μ and below 150μ.

The present invention also provides a preferred particulate bone composition including a particle size distribution of nascent bone particles, allograft bone particles or mixtures or combinations thereof with improved osteogenic capacity or osteoinductive activity, where the distribution includes: (1) from about 1 wt. % to about 10 wt. % of ≧355μ particles, (2) from about 5 wt. % to about 15 wt. % of <355μ and ≧300μ particles, (3) from about 10 wt. % to about 25 wt. % of <300μ and ≧250μ particles, (4) from about 5 wt. % to about 15 wt. % of <250μ and ≧180μ particles, (5) from about 20 wt. % to about 40 wt. % of <180μ and ≧106μ particles, (6) from about 5 wt. % to about 15 wt. % of <106μ and ≧75μ particles, (7) from about 5 wt. % to about 15 wt. % of <75μ and ≧53μ particles, and (8) from about 1 wt. % to about 10 wt. % of <53μ and ≧25μ particles.

Methods

The present invention provides a method including the step of commutating or grinding of bone to form the particulate bone preparations of this invention, where the commutating or grinding is performed under conditions to ensure that a temperature of the bone being ground does not rise above a critical temperature that would reduce, diminish or eliminate its osteoinductive capacity or activity.

The present invention also provides a method for preparing non-demineralized cortical bone, cancellous bone or mixtures or combinations thereof having a desired particle size distribution including the step of commutating frozen or freeze-dried bone for a time and at a temperature sufficient to produce the desired particle size distribution, where the temperature is below a critical temperature known to be detrimental to an osteogenic capacity or osteoinductive activity of bone. The critical temperature is between about 45° C. to about 50° C., which significantly reduces or completely eliminates osteoinductive properties of bone. The commutating step of this invention includes a defined interruption of grinding so that the temperature to which the bone is exposed is carefully controlled so that the temperature of the bone is kept below the critical temperature which would result in a loss of osteoinductive activity. The mill grinder is preferably operated in cycles of about 8 seconds to about 18 seconds. The bone is then sieved for about 14 seconds to about 15 seconds or longer. This allows for sufficient cooling and for the removal of particles having the desired particle sizes according to the compositions of this invention. This method of defined interrupted commutating does not allow the temperature of bone or grinder to rise above about 33° C. from the initial temperature of the bone which is between about 18° C. and about 20° C. The defined interruption process cycle operates for no longer than 3 minutes with an average operating time of about 2.5 minutes being preferred. However, shorter or longer cycles can be employed provided of course that a temperature of the bone and grinder does not rise to or above the critical temperature, which is preferably set at less than or equal to 40° C., particularly, less than or equal to 35° C. and especially less than or equal to 33° C.

The present invention also provides a method repairing bone defects including the step of administering a composition of this invention to a bone defect site of an animal including a human to induce healing of bone defect.

The present invention also provides in vivo and in vitro methods for studying and assessing osteoinductive and toxicity properties of the particulate bone preparations of this invention. The in vivo assays include studies in fully immunocompetent non-human primates. In these animals, a 12×14 mm defect is created in a long bone. The defect is then filled with a bone graft material. The animals are examined at 3 and 6 weeks post-transplantation. The limbs are X-rayed and studied morphologically. The animals were then killed and the bone bearing the transplant was rapidly frozen in liquid nitrogen and then cut with a saw with a diamond blade and photographed. The specimens were then fixed in 10% formalin in Earle's balanced salt solution and decalcified in Pereney's fluid. Paraffin sections were cut and stained with hematoxylin eosin, Masson's trichrome stain and Romanowski-Giemsa stain. The in vitro assay was performed on primary or low-passage cultures of human periosteum or chondrocytes. The latter was employed to detect cytotoxicity (if any) of the preparations.

DESCRIPTION OF THE DRAWINGS

The invention can be better understood with reference to the following detailed description together with the appended illustrative drawings in which like elements are numbered the same:

FIG. 2A is a photograph of a primate femur control with induced bone defects;

FIG. 3 depict a graph of a preferred grinding method for obtaining the preparations of this invention from;

FIGS. 8A-C depict photographs of distal femur having a defect filled with an allograft of this invention 2 weeks post-transplantation;

FIGS. 11A-B depict photographs of distal femur having a defect filled with a cancellous microparticulate bone composition of this invention, 6 weeks post-transplantation;

FIGS. 13A-C depict photographs of distal femur having a defect filled with a powdered demineralized cortical bone allograft 6 weeks post-transplantation; and FIGS. 14A-B depict photographs of proximal tibia having a defect filled with demineralized cortical crushed bone allograft 6 weeks post-transplantation.

DETAILED DESCRIPTION OF THE INVENTION

Figure 1:
FIG. 1 is a photograph of a histologic examination of sections of a bone defect filled with particulate bone allograft, which shows healing and complete replacement of bone allograft particles of this invention with newly formed bone without cartilage components.

The inventors have found that a composition that accelerates release of BMP and/or other growth factors can be constructed based on a unique particle size distribution of natural bone because the particles have multiple surfaces and are inherently three dimensional. The preferred the compositions of this invention have a distribution of particles all below about 355µ with at least 30 wt. % of particles having a particle size of less than 180µ. This particle size distribution provides a unique particulate bone composition of either cancellous bone or cortical bone or mixtures thereof with improved osteoinductive activity. This particulate bone can be effectively used as a single preparation or in mixture with various vehicles such as collagen matrices, viscous chemicals such as hydroxyethyl starch, polyvinyl pyrrolidone etc. The method of bone allograft/xenograft preparation described in the present invention avoids extraction of lipids or inactivation of growth factors and preserves bone composition in its native state. Bearing in mind the uncertainties of rodent animal models the inventors used non-human primates in testing various bone graft preparations. These were implanted intraosseously. In this model bone preparation of certain particle sizes gave unexpectedly superior results compared to other conventional bone grafts.

The present invention is based on the inventors unexpected discovery that Non-demineralized (undecalcified) cortical bone or cancellous bone or mixtures thereof in particle sizes less than about 355µ repeatedly and reliably induces bone formation in defects in bones of non-human primates. Moreover, new bone formation is induced at a rapid rate with direct formation of new osteoid.

The inventors discovered using non-human primate model that this particulate bone preparation generally referred to as particulate bone has a high degree of osteoinductivity of a specific variety, i.e., it induces direct bone formation rather than bone formation through endochondral ossification. The use of non-human primate model with bone being the site of implantation provides information which is applicable to human response, unlike information derived from rodents which can produce heterotopic ossification in response to intramuscular introduction of various bone preparations, matrices or extracts.

The present invention broadly relates to a bone implant composition including a distribution of particles of bone having particle sizes less than or equal to about 355μ and preferably a mixtures of particles having particles sizes between about 355μ and about 250μ, particles having particles sizes between about 250μ and about 150μ, and particles having particles sizes below about 150μ, where the compositions have improved osteoinductive activity or osteogenic capacity.

The present invention broadly relates to a method for making a bone implant composition including a distribution of particles of bone having particle sizes of about 355μ and preferably a mixtures of particles having particles sizes between about 355μ and about 250μ, particles having particles sizes between about 250μ and about 150μ, and particles having particles sizes below about 150μ, where the compositions have improved osteoinductive activity or capacity, where the method includes the step of periodically grinding a bone sample into a composition of this invention, where the periods between each grinding are sufficient to maintain a temperature of the bone below about 33° C.

The present invention broadly relates to a method for treating bone defects including the step of administering one or more therapeutically effective amount of a bone implant composition including a distribution of particles of bone having particle sizes of about 355μ to a bone defect, where composition preferably is a mixtures of particles having particles sizes between about 355μ and about 250μ, particles having particles sizes between about 250μ and about 150μ, and particles having particles sizes below about 150μ, where the compositions have improved osteoinductive activity or capacity.

The present invention also broadly relates to particulate bone composition including a particle size distribution of nascent bone particles, autograft bone particles, xenograft bone particles, allograft bone particles or mixtures or combinations thereof with improved osteoinductive capacity. Preferred distribution are shown in Table I.

particles comprising about 50 wt % of particles having a particle size between about 250μ and about 150μ, about 25 wt % of particles having a particles size between about 150, and about 100μ, and about 25 wt % of particles having a particle size less than about 100μ. A typical composition prepared by according to the method of this invention has a particle size distribution of including:

4.3 wt. % of particles having a particle size of about 355 μ, 11.4 wt. % of particles having a particle size <about 355μ and ≧about 300 μ, 17.4 wt. % of particles having a particle<about 300μ and ≧about 250 μ, 11.2 wt. % of particles having a particle size <about 250μ and ≧about 180 μ, 29.8 wt. % of particles having a particle size <about 180μ and ≧about 106 μ, 8.7 wt. % of particles having a particle size <about 106μ and ≧about 75 μ, 11.7 wt. % of particles having a particle size <about 75μ and ≧about 53μ and 5.2 wt. % of particles having a particle size <about 53μ and ≦≧about 25 μ.

The inventors have shown that micro-particulate bone has superior osteogenic capacity and osteoinductive activity, and in fact, that the smaller the p articles the better the osteoinductive activity. Thus, preferred embodiments of this invention include bone compositions having particle sizes: (a) less than or equal to about 355μ, (b) less than or equal to 300μ, (c) less than or equal to 250μ, (d) less than or equal to 180μ, (e) less than or equal 106μ, (f) less than or equal to 75μ, (g) less than or equal to 53μ and (h) less than or equal to 25μ. The inventors believe that compositions having smaller particles sizes or particle size distributions including smaller sized particles have superior osteogenic capacity and superior osteoinductive activity.

The osteogenic capacity or osteoinductive activity of the preparations of this invention are thought by the inventors to

TABLE I

Preferred Particle Size Distributions

| Particle Size | Broader Range | Moderate Range | Narrower Range |
|---|---|---|---|
| ≧355 μ | 1 wt. % to 10 wt. % | 2.5 wt % to 7.5 wt. % | 3 wt % to 6 wt. % |
| <355 μ and ≧300 μ | 5 wt. % to 15 wt. % | 7.5 wt % to 12.5 wt. % | 9 wt % to 12 wt. % |
| <300 μ and ≧250 μ | 10 wt. % to 25 wt. % | 12.5 wt % to 22.5 wt. % | 15 wt % to 20 wt. % |
| <250 μ and ≧180 μ | 5 wt. % to 15 wt. % | 7.5 wt % to 12.5 wt. % | 9 wt % to 12 wt. % |
| <180 μ and ≧106 μ | 20 wt. % to 50 wt. % | 22.5 wt % to 47.5 wt. % | 25 wt % to 45 wt. % |
| <106 μ and ≧75 μ | 5 wt. % to 15 wt. % | 7.5 wt % to 12.5 wt. % | 9 wt % to 12 wt. % |
| <75 μ and ≧53 μ | 5 wt. % to 15 wt. % | 7.5 wt % to 12.5 wt. % | 9 wt % to 12 wt. % |
| <53 μ and ≧25 μ | 1 wt. % to 10 wt. % | 2.5 wt % to 7.5 wt. % | 3 wt % to 6 wt. % |

From Table I, it is obvious that the preferred composition include a particle size distribution including at least 31 wt. % of particles have a diameter less than 180μ, preferably at least 40 wt. % of particles have a diameter less than 180μ, and preferably at least 46 wt. % of particles have a diameter less than 180μ. Alternatively, the compositions have a particle size distribution including between about 30 wt. % and about 75 wt % of particles have a diameter less than 180μ, preferably, between about 35 wt. % and about 60 wt. % of particles have a diameter less than 180μ and particularly, between about 40 wt. % and about 50 wt. % of particles have a diameter less than 180μ. One preferred embodiment of the composition of this invention includes a distribution of depend primarily on particle size and retention of unaltered growth factors and other substances. The osteogenic capacity or osteoinductive activity of either cortical bone or cancellous bone or mixtures thereof decreases if particles exceed the range of 355μ. Likewise exposure of the same preparations to hydrogen peroxide, ethyl alcohol or isopropyl alcohol markedly decreases its osteoinductive capacity. The invention is directed to the method of preparation of non-demineralized osteoinductive bone particles as well as to the clinical application of these preparations.

It has been demonstrated that the preparations of this invention that comprise a defined particle size distribution of particulate cortical bone or cancellous bone or mixtures thereof exert osteoinduction in the skeletal structures of higher animals namely non-human primates. This animal model, unlike rodent models, which produce heterotopic bone formation in the muscles, is closest to humans. Thus, it can be anticipated that response to the particulate bone preparations of this invention in humans will be similar to that in non-human primates.

The present invention is directed to implants for stimulating osteoinduction, bone regrowth, and/or bone repair by the implantation of a particulate bone preparation of this invention in a bone defect in an animal including a human. Moreover, the present invention can include particulate bone that has been treated with additional bone growth factors to further enhance and improve bone regeneration after implantation.

The process of particulate bone preparation is equally applicable to allogeneic and xenogeneic bone. The particulate bone preparations of this invention are unique because they avoid entirely the need for harsh chemical treatments and extractions, which alter inherent native properties of bone. The particulate bone preparations of this invention can be produced either from freeze-dried bone not subjected to any chemical treatment or from frozen bone. The invention permits reproducible production of a particulate bone preparation with optimal osteoinductivity clearly demonstrable in higher animal models.

EXPERIMENTAL SECTION OF THE INVENTION

Histologic examination of bone sections filled with particulate bone showed significant healing and complete replacement of bone allograft particles with newly formed bone six weeks post implantation without cartilage components as shown in FIG. 1. The term significant healing for the purposes of this application means that newly formed bone is evident throughout the implant six weeks post implantation. Gross photographs likewise show healing and replacement of the defects with normal trabecular bone of particulate allografts packed into a bone defect as shown in FIG. 2. Untreated defect remains unhealed, while bone defect packed with autologous bone likewise shows healing, as expected. Bone defect packed with allografts measuring about 1 mm across shows retention of unincorporated bone graft particles.

Preparation of Particulate Bone Particles Measuring Less Than 355 μ

The present invention prepares particulate cortical bone or cancellous bone or mixtures thereof without "undesirable constituents." For the purposes of the present invention the term "undesirable constituents" means any constituent other than osteoid tissue normally present in bone or bone marrow. This includes blood, bone marrow, free fat and soft connective tissue elements.

Detailed Description of the Preparation of the Particulate Bone

Particulate bone of a powdery consistency can be prepared from previously freeze-dried cortical bone or cancellous bone or mixtures thereof. After freeze-drying and associated processing which includes repeated washing in warm saline or other balanced salt solutions to remove "undesirable constituents", the bone is immersed directly into liquid nitrogen vapor and is then freeze-dried in accordance with previously published procedures (Malinin 1, 2, 3) to a residual moisture of 5 to 6% or less. Residual moisture content was determined gravimetrically.

Freeze-dried bone is cut into cubes with a band saw, an oscillating or a rotary saw without heating the bone preparation, by avoiding pressure on the bone being cut and by limiting the time of grinding to no more than 15 second for each surface being cut.

Cut bone cubes, rectangles or other small configurations are further cut in a turbo mill, micro hammer cutter mill, disc mill, toothed disc mill, jet mill or other similar mills capable of grinding bone or reducing bone to particles having a particle size less than about 355μ. Although usually dry bone is ground, cutting of wet bone preparation can be also accomplished.

Any grinding process is associated with heat production. Heating bone above about 45° C. to about 50° C. is undesirable as the heat significantly reduces to completely abolishes osteoinductive properties of bone. Continuous grinding for 3 to 5 minutes in any of the conventional grinding mills will raise the temperature to 70° C. or above. The inventors have devised a method for defined interrupted grinding so that the temperature exposure to the bone can be carefully controlled and kept below a temperature which would not result in a loss of osteoinductive activity. The mill is operated in cycles of about 8 seconds to about 18 seconds, then the bone is sieved a duration of about 14 seconds to about 15 seconds. This does not allow the temperature of bone or grinder to rise above about 33° C. from the initial temperature of the product of between about 18° C. and about 20° C. The cycle operates for no longer than 3 minutes with an average operating time of about 2.5 minutes. The results of typical temperature profiles of bone being ground and that of the grinder and its components are shown graphically in FIG. 3.

Figure 4:
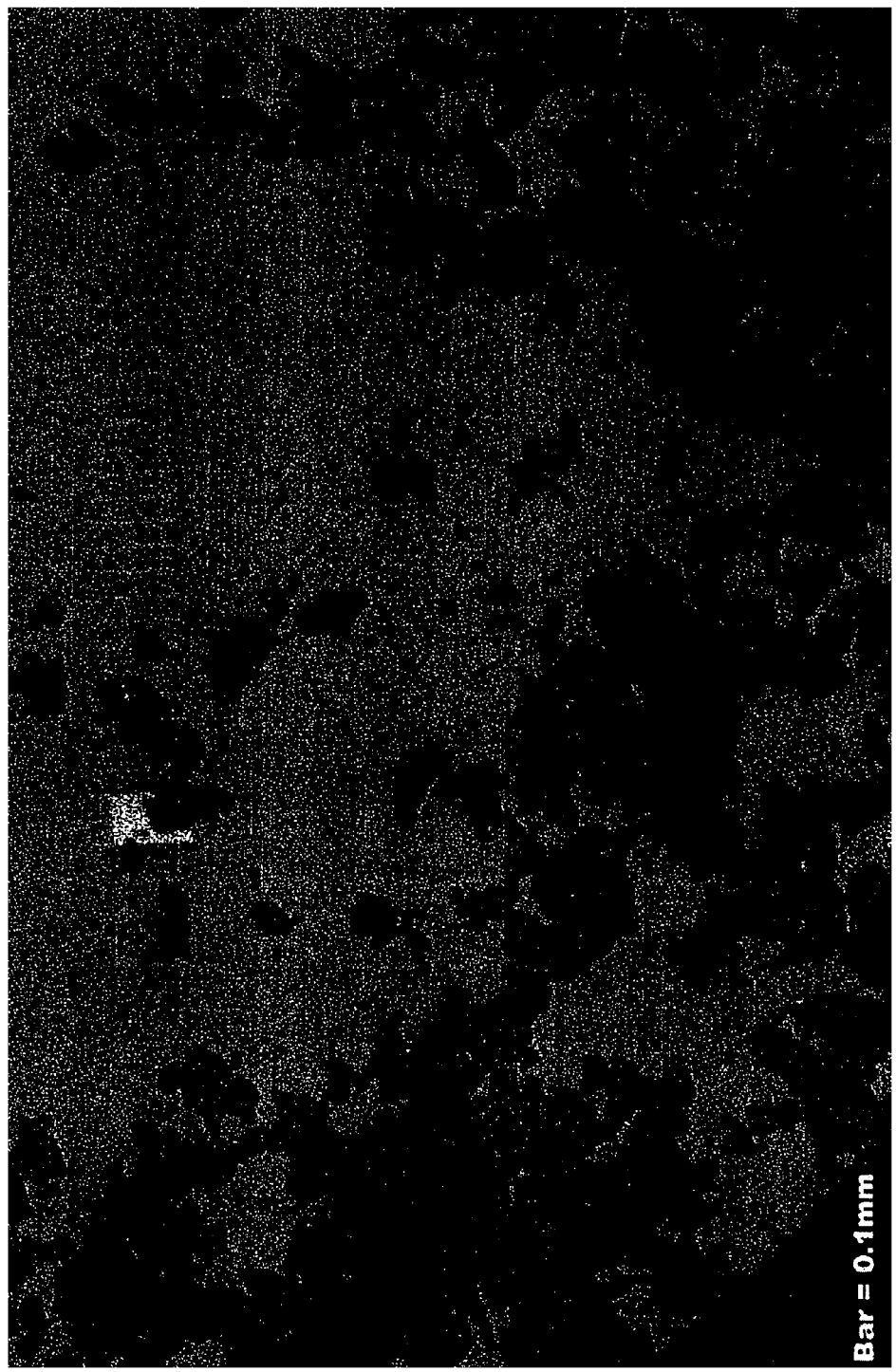
FIG. 4 is a photograph of bone particles having a particle size of 150µ or less.
Figure 5A:
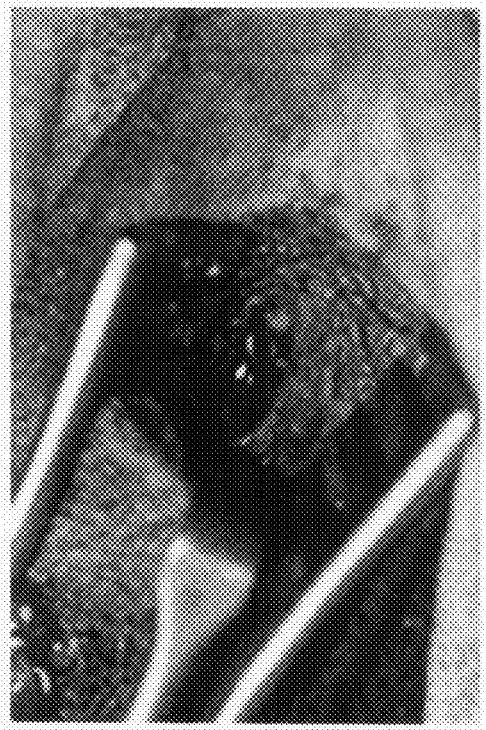
FIGS. 5A-D depict non-human primate bone site preparation and implantation of allografts.
Figure 5B:
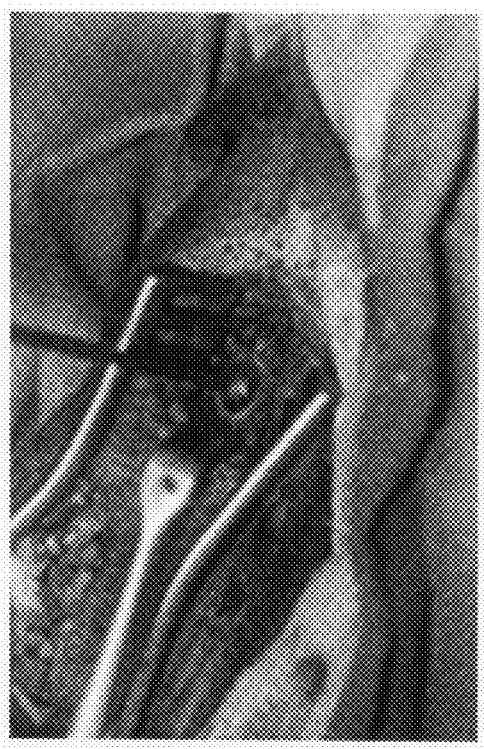
Figure 5C:
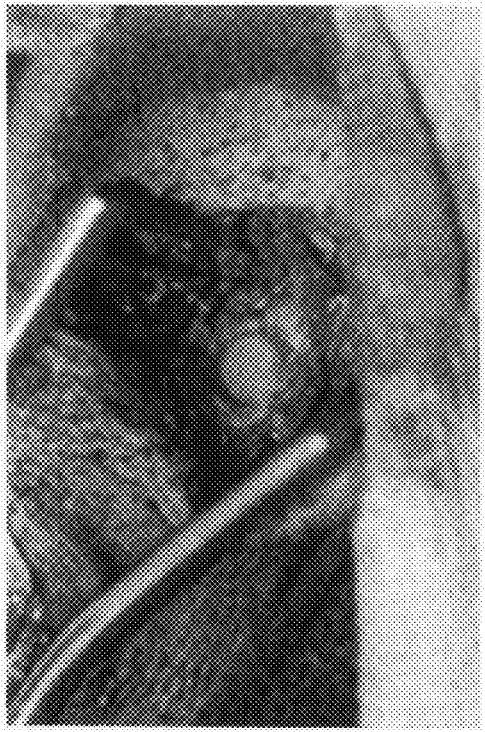
Figure 5D:
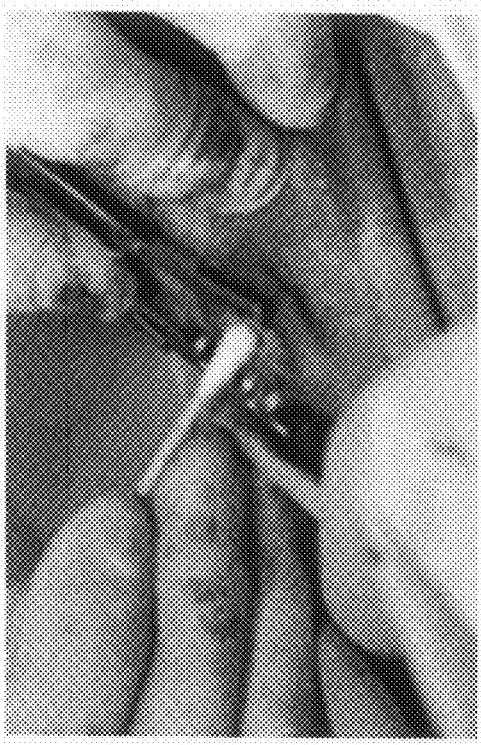

The above described procedures of repeated grinding and sieving allows for the preparation of specific formulation of non-decalcified particulate bone preparations with high osteoinductive properties. One preferred embodiment of this invention includes compositions having a particle size distributions as follows: (1) from about 24.6 wt % to about 36.3 wt % of particles having a particle size between about 350μ and about 250 μ; (2) 22 wt % to about 25 wt % of particles having a particle size between 25μ and about 150 μ; and (3) from about 36.7 wt % to about 46.7 wt % of particles having a particle size less than 150μ. Particularly, the particles having a particle size below about 25μ should have the following distribution: 35-65 wt % of particles having a particle size between about 250μ and about 150μ, about 10 wt % to about 40 wt % of particles having a particles size between about 150μ and about 100μ, and about 10 wt % to about 40 wt % of particles having a particle size less than about 100μ. More particularly, the particles having a particle size below about 250μ should have the following distribution: 40 wt % to about 60 wt % of particles having a particle size between about 250μ and about 150μ, about 15 wt % to about 35 wt % of particles having a particles size between about 150μ and about 100 g, and about 15 wt % to about 35 wt % of particles having a particle size less than about 100μ. Especially, the particles having a particle size below about 250μ should have the following distribution: 50 wt % of particles having a particle size between about 250μ and about 150μ, about 25 wt % of particles having a particles size between about 150μ and about 100μ, and about 25 wt % of particles having a particle size less than about 100μ. Particles less than 150μ are shown in the photograph of FIG. 4.

DETAILED EXPLANATION OF FIGURES

Referring now to FIG. 1, a histological section of a non-human primate bone defect filled with particulate non-decalcified bone. New bone is formed around vascular channels filled with mesenchymal tissue. Osteoblasts are present in the channels. There is no cartilage formation. This means there is a complete regeneration and bone replacement without newly formed bone going through the endochondral ossification stage.

Referring now to FIG. 2A, a cut section of femur six weeks after creation of a defect used in the study. The defect remains largely unhealed with new bone forming only at the edges of the defect. The defect is marked with a 1.

Figures 2B, 2C:
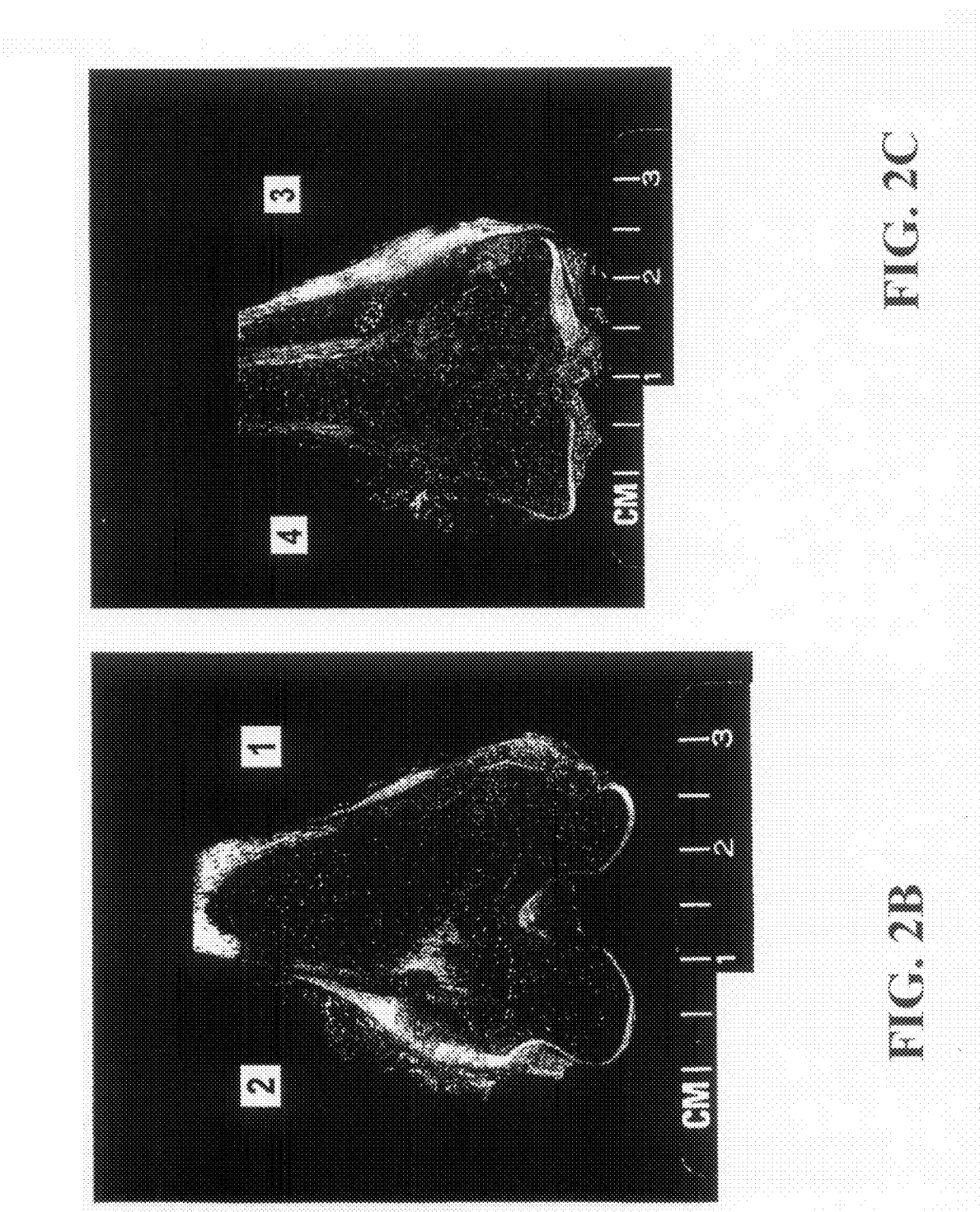
FIG. 2B is a photograph of a primate femur after the defects have been treated with a bone replacement composition: 1 is defect filled with a composition of this invention and 2 is a defect filled with a conventional allograft.
FIG. 2C is a photograph of a primate tibia after the defects have been treated with a bone replacement composition: 4 is a defect filled with a composition of this invention and 3 is a defect filled granular bone implant.

Referring to FIGS. 2B&C, cut sections of the femur and the tibia with bone defects filled with preparations under study. Numbers 1 and 4 designate defects filled with a particulate preparation that is not demineralized. The defects are completely healed and replaced with newly formed trabecular bone. Number 2 is a defect filled with an autograft. The defect is partially filled with sclerotic bone. Number 3 is defect filled with granular bone. Graft particles are still visible and the defect is only partially filled.

Figure 3:
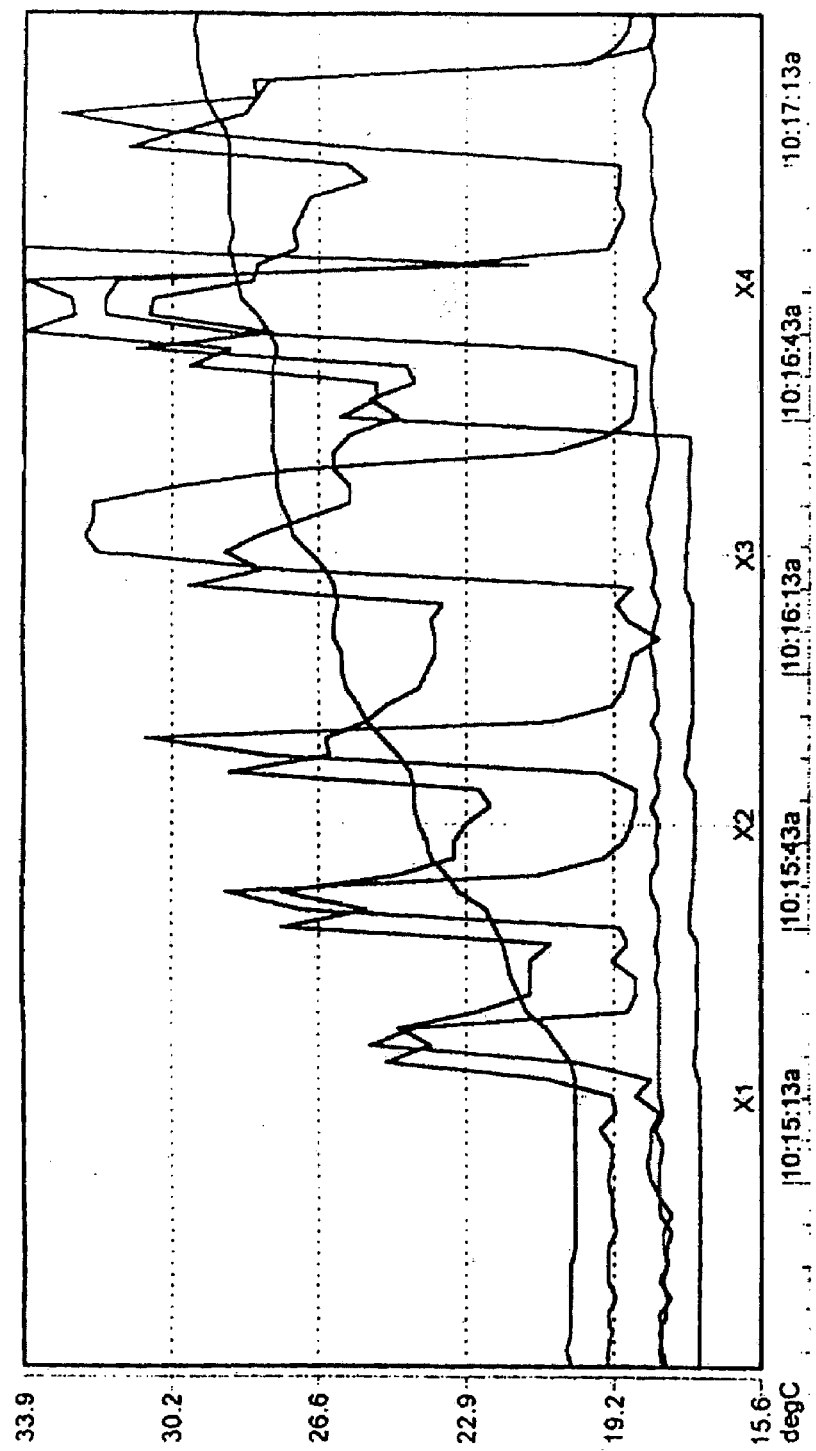

Referring to FIG. 3, a graph is shown that illustrates temperature profiles during grinding of the bone. Red line represents the temperature in the wall of the grinder, blue inside the grinder. Green represents the temperature in the bone being ground. Purple is the temperature of the grinding port. Fuchia, room temperature. The graph illustrates vividly the necessity for grinding the bone in intervals of some 25 seconds to avoid overheating and deactivating the osteoinductive properties of the preparations.

Referring now to FIG. 4, a photomicrograph of particles smaller than 150 µ. Each interval between lines is 0.1 mm.

New Experimental Data

These examples illustrate a study of bone allograft particles size in relation to healing of bone defects in non-human primates.

Ideal size of particulate bone used to fill osseous defects has not been determined. Likewise, the osteoinductive properties of deminerialized and non-demineralized particulate bone have not been compared in a non-human primate model. Information obtained from rodent model studies might not be directly applicable to humans because osteoinductive capacity of bone allografts in rodents is measured by the formation of heterotopic bone. Humans and higher animals do not respond to extraosseous particulate allograft implantation by forming heterotopic bone. Thus, the inventors have studied the healing of experimentally induced bone defects in non-human primates packed with various particulate bone allograft preparations. These bone preparations were freeze-dried, non-demineralized and demineralized. Frozen particulate bone was also tested.

Studies were performed on 24 adult, young male baboon (*Papio hymadryas*). Bone allografts were excised and processed under aseptic conditions. Particulate alllografts were prepared in three different particles size distributions: 1) all particles less than 250µ, referred to as "bone powder" in these examples; 2) particles between 500µ and 800µ, referred to as "ground bone" in these examples; and 3) particles between 1 mm and 2 mm, referred to as "crushed bone" in theses examples. Both non-demineralized and demineralized allografts were freeze-dried after freezing in liquid nitrogen vapor. Frozen preparations were ground in the frozen state to minimize heating as set forth above.

Bone allografts were placed in 10 mm diameter defects made with a burr in the distal femurs and proximal tibias of the right leg in AP or medial-lateral planes as shown in FIGS. 5A-D. Three or four defects were created in each animal. Control detects were left unfilled. Positive controls were filled with autografts. The soft tissue and skin were closed in layers with Vicryl sutures and after recuperation, the animals were returned to their enclosures without limitations of physical activity.

Animals were sacrificed at 2 to 3 weeks or at 6 weeks or at six weeks postopertion.

Referring now to FIGS. 5A-D, the surgical procedure for forming the filling the defects in the femur or tibia of a baboon is shown. Look at FIG. 5A, an opening is made in the distal femur or proximal tibia with a 10 mm diameter burr to a depth of 15 mm. The defects are randomly placed in the medio-lateral or AP direction. Looking at FIG. 5B, profuse bleeding from the medullary canal usually occurs. Looking at FIG. 5C, bone allografts was packed into the defect. Looking at FIG. 5D, in the case of allografts comprised of non-demineralized bone powder (i.e., microparticulate bone), the bone powder allografts produced hemostatis after being packed into the defect.

Figure 6A:
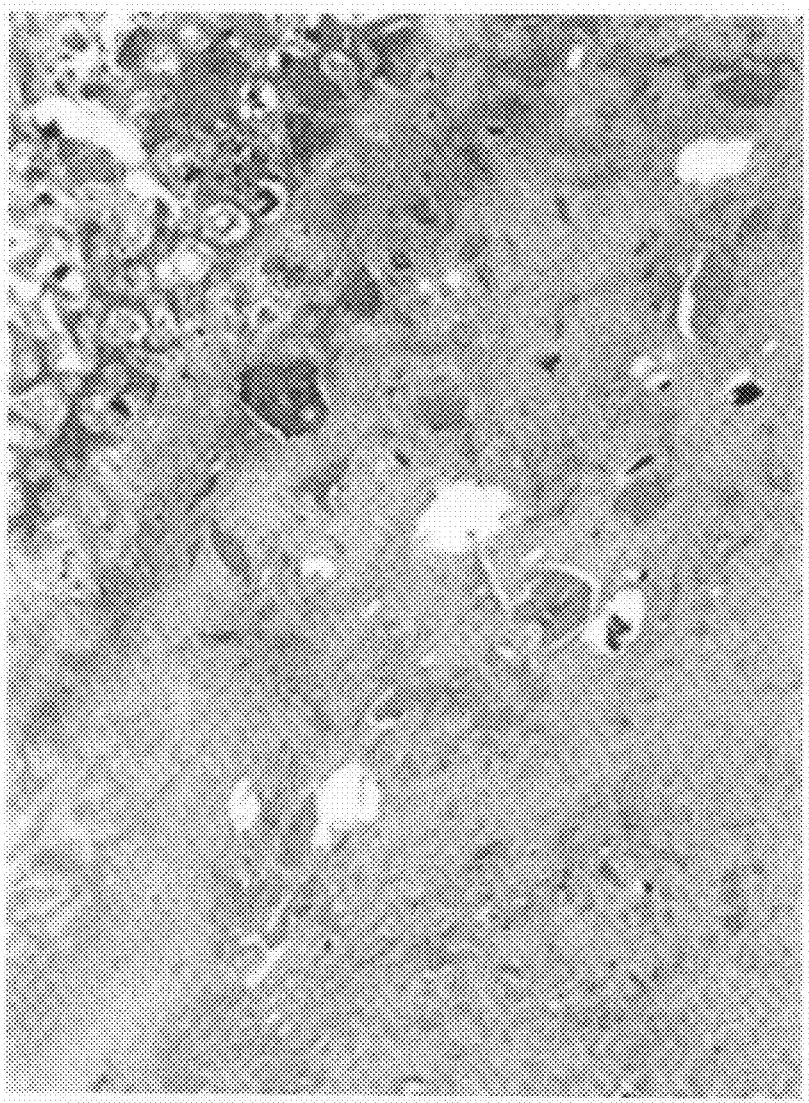
FIGS. 6A&B depict photographs of a control group distal femur having a defect 6 weeks postoperative.
Figure 6B:
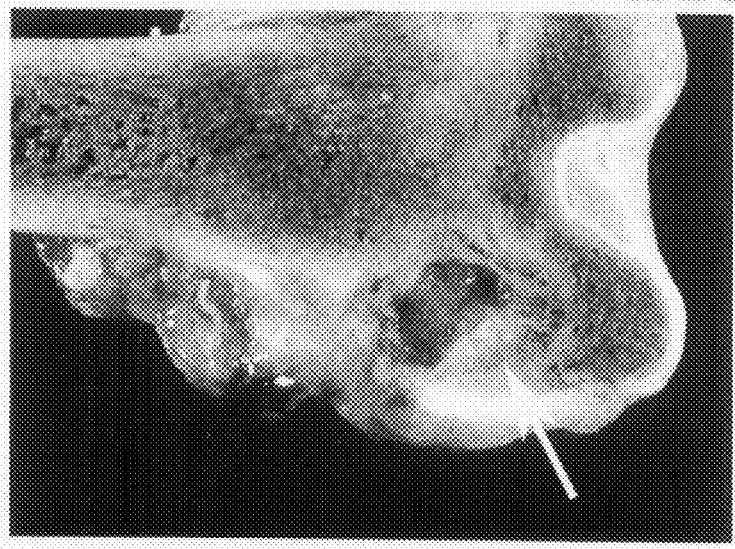

Referring to FIG. 6A, a section of the femur from a control animal is shown. The defect has not healed six weeks postoperative, but there was some new, reactive bone formation in the periphery. A histological section showed new bone formation in the depth of the defect as shown in FIG. 6B.

Figure 7B:
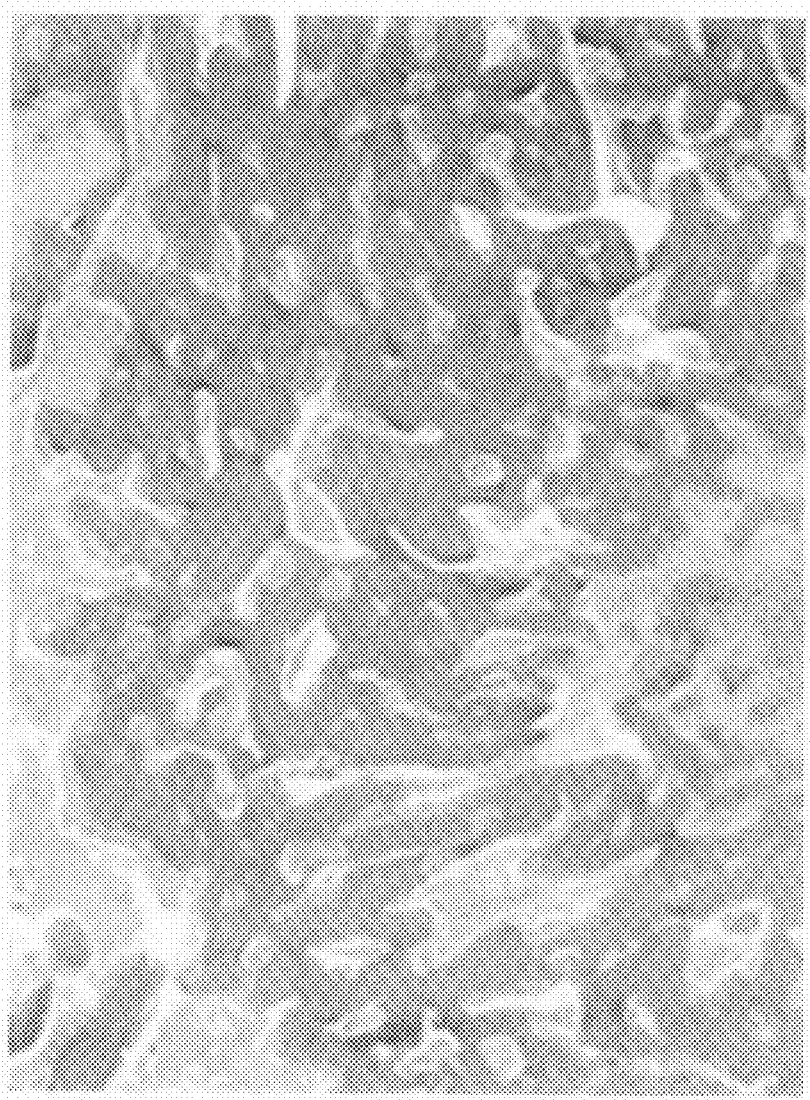
FIGS. 7A&B depict photographs of distal femur defect filled with an autograft, 6 weeks post-transplantation.
Figure 7A:
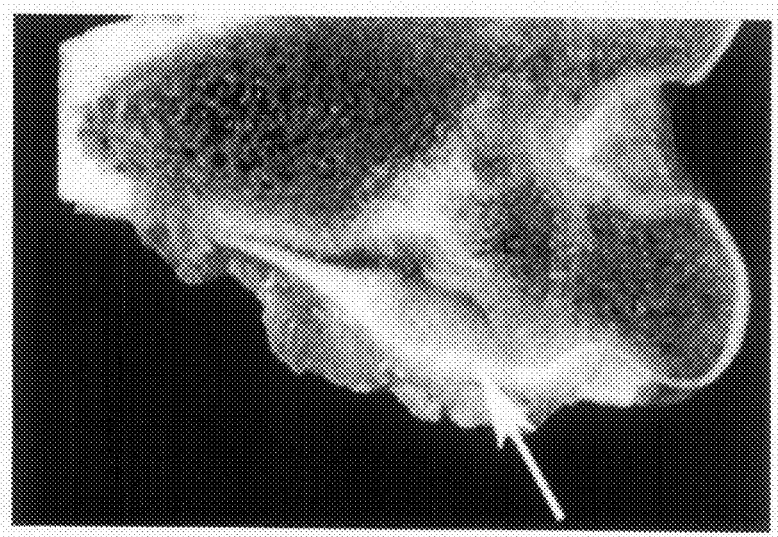

Referring to FIG. 7A, a section of bone including a defect filled with a microparticulate bone allograft showed that the defect was almost entirely filled with new bone. A histological section from the periphery showed an allograft filled defect as shown in FIG. 7B.

Referring to FIG. 8A, a section of femur having a defect filled with a cortical bone allograft is depicted 2 week post transplantation, where the allograft comprises bone powder. The bone cut was made through the periphery of the defect. A histological section through the defect showed that in the center of the defect there are densely packed bone allograft particles with retained osteoid as shown in FIG. 8B. In the periphery, there is intense osteogenic activity with the formation of new bone, where the bone particles of the transplant are surrounded by new bone with intense, simultaneous osteoclastic and osteoblastic activity as shown in FIG. 8C.

Figure 9A:
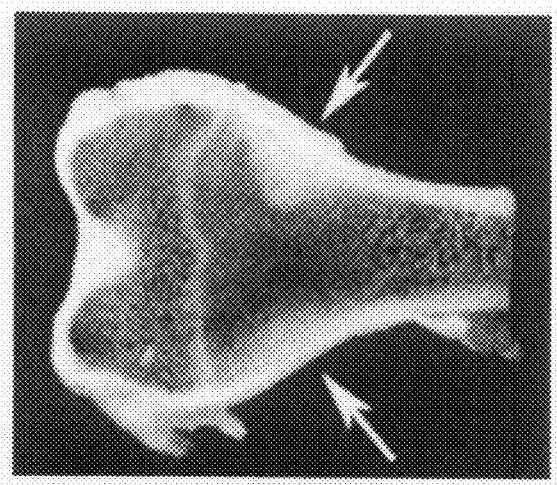
FIGS. 9A-C depict photographs of distal femur having a defect filled with a cortical microparticulate bone composition of this invention, 6 weeks post-transplantation.
Figure 9B:
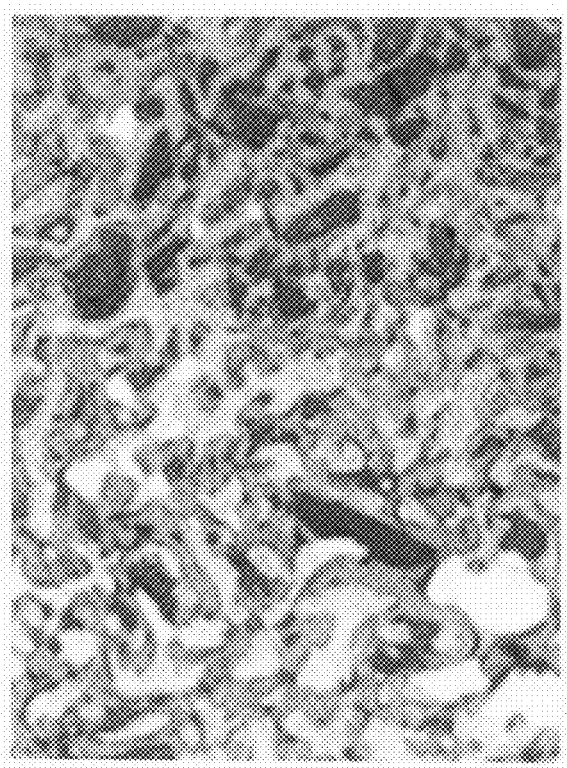
Figure 9C:
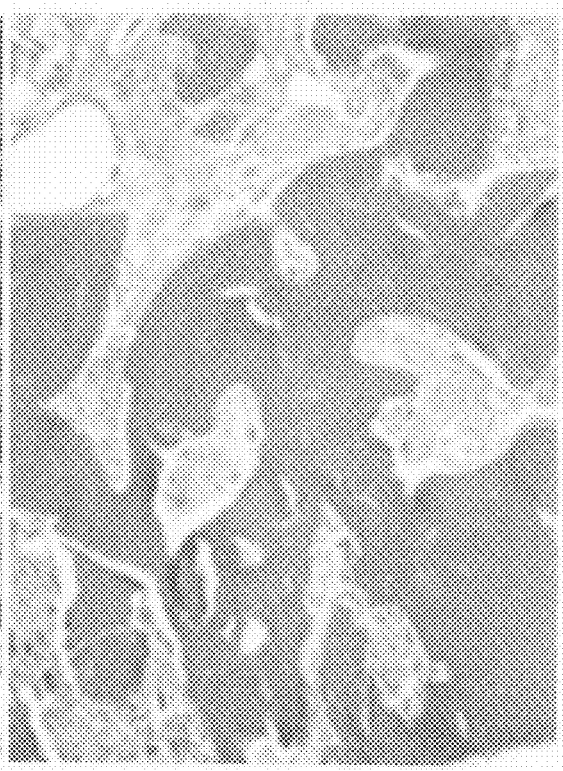

Referring to FIG. 9A, a section of the distal femur with defects in which cortical bone powder was packed is shown. Both defects are now filled with new bone. A histological section showed incorporation of densely packed bone allograft particles into newly formed bone as shown in FIG. 9B. Another histological section showed bone particles which have been replaced with new bone, revascularized and repopulated with osteocytes as shown in FIG. 9C.

Figure 10C:
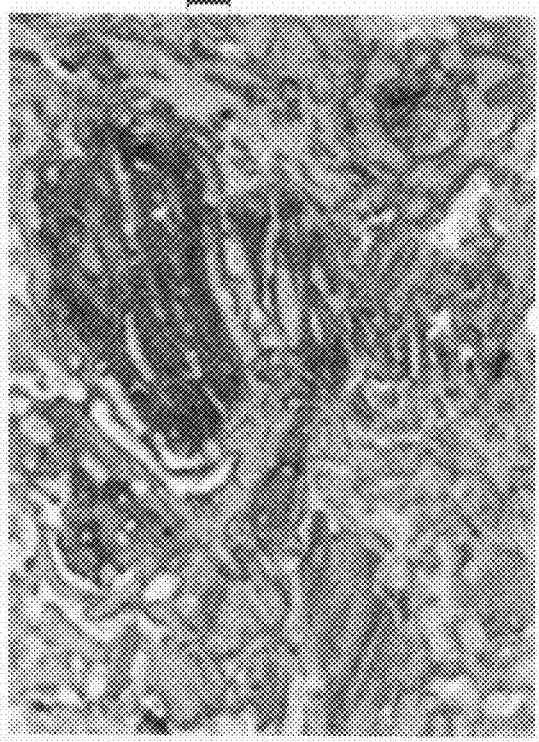
FIGS. 10A-C depict photographs of distal femur having a defect filled with a cortical ground bone material, 6 weeks post-transplantation.
Figure 10B:
Figure 10A:
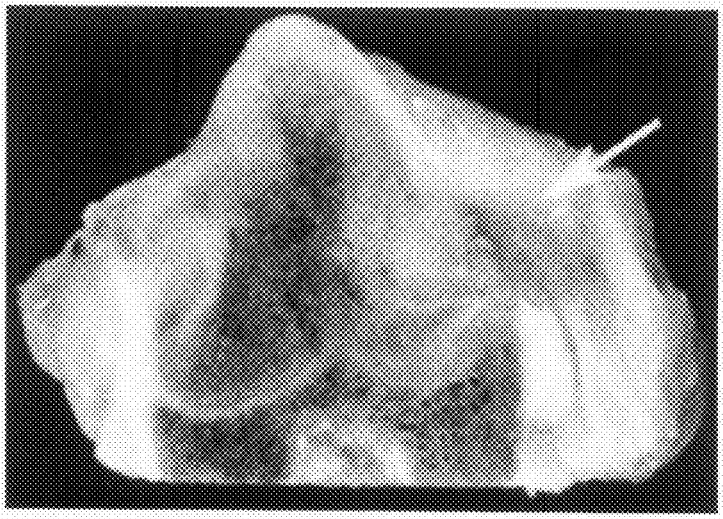

Referring to FIG. 10A, a section of distal femur with a defect filled with ground cortical bone allograft is shown. A histological section showed that bone allograft pieces are widely separated and there is only a minimal amount of osteogenesis at the edges as shown in FIG. 10B. Another histological section showed that in the periphery new bone formation around large allograft particles is evident as shown in FIG. 10C.

Referring to FIG. 11A, a section of distal femur with a defect filled with cancellous bone powder was completely healed. A histological section showed newly formed bone reminiscent of callus as shown in FIG. 11B.

Figure 12C:
FIGS. 12A-D depict photographs of distal femur having a defect filled with powdered demineralized cortical bone 3 weeks post-transplantation.
Figure 12D:
Figure 12B:
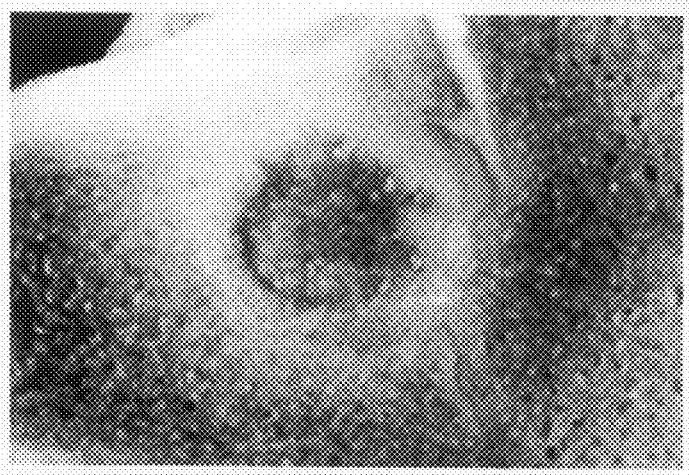
Figure 12A:
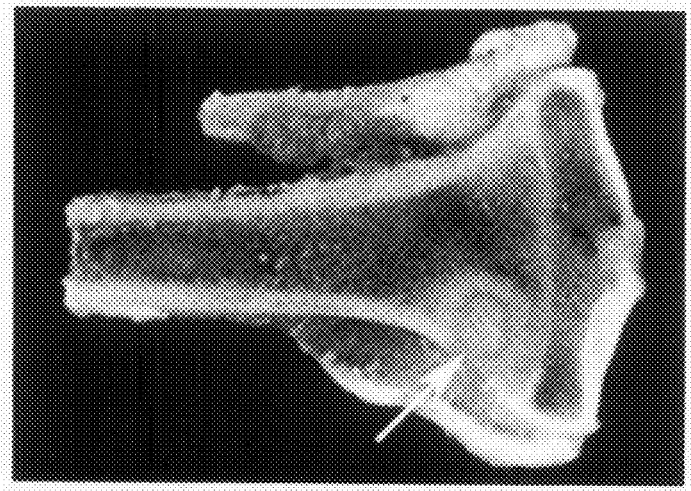

Referring to FIGS. 12A-B, a section of distal femur with a defect filled with demineralized cortical bone powder three weeks post transplantation is shown, where the defect remains unhealed. Allograft material is plainly visible in the gross specimen as shown in FIGS. 12A&B and in the radiograph as shown in FIG. 12C. A histological section showed unaltered allograft material in the center of the defect and a layer of mesenchymal tissue between the allograft and newly formed bone as shown in FIG. 12D.

Referring to FIG. 13A, a section of distal femur with a defect filled with demineralized cortical bone powder allograft is shown, where the defect is surrounded by a cuff of newly formed bone. Histological sections evidenced endochondral bone formation at the graft-host junction as shown in FIGS. 13B&C.

Referring to FIG. 14A, a section of proximal tibia with a defect filled with demineralized cortical crushed bone six weeks post transplantation is shown, where intense bone formation peripheral to the graft is evident. A histological section showed a large allograft particle surrounded by new bone as shown in FIG. 14B.

Results

The control defects were filled with fibrous connective tissue, but remained unhealed six weeks postoperative. However, rims of newly formed bone were evident at the edges of the defects. Defects packed with particulate autografts were filled with newly formed cancellous bone. At two weeks, defects filled with microparticulate cortical bone allograft showed unaltered bone allograft particles in the center of the defect, and bone particles surrounded by osteoblasts and osteoblasts in the periphery. By six weeks, the defects were filled entirely with newly formed bone. Bone defects packed with cortical ground bone had clearly recognizable (macroscopic and microscopic) bone particles in the defect with early osteogenesis in the periphery. Defects packed with cortical crushed bone were similar in appearance to those packed with ground bone allografts.

Microparticulate cancellous bone allograft behaved in the same manner as did microparticulate cortical bone allograft. At six weeks, cancellous bone particles formed a new network bone with particles themselves surrounded by newly formed bone and repopulated with osteocytes. Active osteogenesis as evidenced by rims of osteoblasts surrounding the allograft particles was present. At three weeks, demineralized cortical bone particles placed in a defect were intact. There was only a thin rim of newly formed bone in the periphery, but this was separated from the allograft by a sleeve of mesenchymal tissue. At six weeks, there was clear evidence of endochondral bone formation in the periphery of the allograft mass. Demineralized crushed bone at six weeks had distinct particles with virtually no new bone formation except in the periphery as did cortical crushed bone allografts.

Discussion

The data showed a clear difference in the healing pattern of bone allografts in relationship to the size of the graft particles. The most complete and rapid healing was achieved with freeze-dried microparticulate cortical and cancellous bone allografts, i.e., allografts comprising micron sized particles. This type of graft was easy to pack into the defect cavity and to obliterate the defect. The bone powder grafts were hemostatic and highly osteogenic. The allografts incorporated by direct ossification. Allografts with larger particles (ground or crushed cortical bone) were difficult to impact and thus would not completely obliterate the defect. Although these two forms were osteogenic, the healing associated with these grafts was much slower than observed with the microparticulate bone grafts. No difference was noted between microparticulate cancellous and cortical bone preparations.

Results with demineralized bone allografts having comparable particles sizes to the non-demineralized allografts were disappointing. With these latter allografts, new bone formation was induced primarily only in the periphery. When demineralized allograft particles were replaced, endochondral ossification was noted.

Conclusion

Incorporation of particulate bone allografts is dependent on the size of the particles in the grafts and the method of its preparation. Freeze-dried, microparticulate cortical bone allografts first provide biomechanical support and most rapid healing of the defect into which they are placed. They incorporate by direct ossification, thus producing rapid new bone formation. Demineralized cortical bone powder allografts stimulate the surrounding bone, but by themselves do not undergo accretion. Healing from the periphery is accomplished via as lower process of endochondral ossification.

Closing

All references cited herein are incorporated by reference. While this invention has been described fully and completely, it should be understood that, within the scope of the appended claims, the invention may be practiced otherwise than as specifically described. Although the invention has been disclosed with reference to its preferred embodiments, from reading this description those of skill in the art may appreciate changes and modification that may be made which do not depart from the scope and spirit of the invention as described above and claimed hereafter.

We claim:

1. A composition for use as a bone implant comprising particulate bone including particles having sizes less than or equal to about 355 µm and having a particle size distribution including from about 24.6 wt % to about 36.3 wt % of particles having a particle size between about 350 µm and about 250 µm, from about 22 wt % to about 25 wt % of particles having a particle size between 250 µm and about 150 µm, and from about 36.7 wt % to about 46.7 wt % of particles having a particle size less than 150 µm, and prepared from bone having an initial temperature between about 18° C. and about 20° C. and ground in a mill under conditions so that the bone is not heated above a critical temperature of less than or equal to 40° C., where the particulate bone is non-chemically extracted, non-demineralized, and where said composition has improved osteoinductive activity and regeneration of bone defects as compared to demineralized particulate bone.

2. The composition of claim 1, further comprising a particle size distribution of particles having sizes between about 25 µm and about 355 µm.

3. The composition of claim 2, wherein the particle size distribution includes about 50 wt % of particles having a particle size between about 250 µm and about 150 µm, about 25 wt % of paticles having a particles size between about 150 µm and about 100 µm, and about 25 wt % of particles having a particle size less than about 100 µm.

4. The composition of claim 1, wherein the particulate bone is particulate cortical bone, particulate cancellous bone or mixtures or combinations thereof.

5. The composition of claim 1, wherein the bone is selected from the group consisting of autograft bone, allograft bone, xenograft bone and mixtures or combinations thereof.

6. The composition of claim 1, wherein the particles having a particle size below about 250 μm, comprise:
   from about 35 wt % to 65 wt % of particles having a particle size between about 250 μm and about 150 μm,
   from about 10 wt % to about 40 wt % of particles having a particles size between about 150 μm, and about 100 μm, and
   from about 10 wt % to about 40 wt % of particles having a particle size less than about 100 μm.

7. The composition of claim 1, wherein the particles having a particle size below about 250 μm comprise:
   from about 40 wt % to about 60 wt % of particles having a particle size between about 250 μm and about 150 μm,
   from about 15 wt % to about 35 wt % of particles having a particles size between about 150 μm and about 100 μm, and
   from about 15 wt % to about 35 wt % of particles having a particle size less than about 100 μm.

8. The composition of claim 1, wherein the particles having a particle size below about 250 μm comprise:
   about 50 wt % of particles having a particle size between about 250 μm and about 150 μm,
   about 25 wt % of particles having a particles size between about 150 μm and about 100 μm, and
   about 25 wt % of particles having a particle size less than about 100 μm.

9. A method for making a particulate bone composition according the claim 1, comprising the step of grinding non-chemically extracted and non-demineralized bone having an initial temperature between about 18° C. and about 20° C. in a mill, while maintaining the bone at a temperature at or below a critical temperature of less than or equal to 40° C. to produce the praticulate bone composition comprising particles having sizes less than or equal to about 355μm, where the temperature reduces damage to the bone, and where the particulate bone composition has improved osteoinductive activity and regeneration of bone defects as compared to demineralized particulate bone.

10. The method of claims 9, wherein the critical temperature is 40° C.

11. The method of claim 9, wherein the critical temperature is 35° C.

12. The method of claim 9, wherein the critical temperature is 33° C.

13. The method of claim 9, wherein the bone, prior to commutating, is selected from the group consisting of dry bone, wet bone, freeze-dried bone, frozen nascent bone, and mixtures or combinations thereof.

14. The method of claim 9, wherein the bone is selected from the group consisting of autografe bone, allograft bone, xenograft bone and mixtures or combinations thereof.

15. A method for making a particulate bone composition according the claim 1, comprising the step of grinding non-chemically extracted and non-demineralized bone having an initial temperature between about 18° C. and about 20° C. for a first period of time to form crude particulate bone composition in a mill; sieving the crude particulate bone composition for a second period of time to form sieved particulate bone composition; and repeating the grinding and sieving steps for a third period of time sufficient to produce the particulate bone composition comprising particles having sizes less than or equal to about 355 μm, where the grinding and sieving steps are performed so that a temperature to which the bone is exposed is maintained below a critical temperature of less than or equal to 40° C. to reduce or eliminate loss of osteoinductive activity, and where the particulate bone composition has improved osteoinductive activity and regeneration of bone defects as compared to demineralized particulate bone.

16. The method of claim 15, wherein the first period of time is between about 8 seconds and about 18 seconds.

17. The method of claim 15, wherein the second period of time is between about 14 seconds and about 15 seconds or longer.

18. The method of claim 15, wherein the third period of time is about 3 minutes.

19. The method of claim 15, wherein the third period of time is about 2.5 minutes.

20. The method of claims 15, wherein the critical temperature is 40° C.

21. The method of claim 15, wherein the critical temperature is 35° C.

22. The method of claim 15, wherein the critical temperature is 33° C.

23. The method of claim 15, wherein the bone, prior to commutating, is selected from the group consisting of dry bone, wet bone, freeze-dried bone, frozen nascent bone, and mixtures or combinations thereof.

24. The method of claim 15, wherein the bone is selected from the group consisting of autograft bone, allograft bone, xenograft bone and mixtures or combinations thereof.

25. A method for treating bone defects comprising the step of implanting a therapeutically effective amounts of a particulate bone composition according to claim 1, including non-chemically extracted and non-demineralized particulate bone into a bone defect of an animal including a human, where the composition has improved osteoinductive activity as compared to demineralized particulate bone, and where the composition induces healing of the bone defect via the implantation of said composition into said defect.

26. The method of claim 25, wherein the composition induces significant healing of the defect six week post implantation.

27. The method of claim 25, further comprising a particles size distribution of particles having sizes between about 25μ and about 335μ.

28. The method of claim 27, wherein the distribution includes:
   from about 24.6 wt % to about 36.3 wt % of particles having a particle size between about 350 μm and about 250 μm;
   from about 22 wt % to about 25 wt % of particles having a particle size between 250 μm and about 150 μm; and
   from about 36.7 wt % to about 46.7 wt % of particles having a particle size less than 150 μm.

29. The method of claim 28, wherein the particles having a particle size below about 250μ comprise:
   from about 35 wt % to 65 wt % of particles having a particle size between about 250 μm and about 150 μm,
   from about 10 wt % to about 40 wt % of particles having a particles size between about 150 μm and about 100 μm; and
   from about 10 wt % to about 40 wt % of particles having a particle size less than about 100 μm.

30. The method of claim 28, wherein the particles having a particle size below about 250μ comprise:
   from about 40 wt % to about 60 wt % of particles having a particle size between about 250 μm and about 150 μm, from about 15 wt % to about 35 wt % of particles having a particle size between about 150 μm and about 100 μm, and from about 15 wt % to about 35 wt % of particles having a particle size less than about 100 μm.

31. The method of claim 28, wherein the particle having a particle size below about 250 μm comprise:

about 50 wt % of particles having a particle size between about 250 μm and about 150 μm, about 25 wt % of particles having a particle size between about 150 μm and about 100 μm, and from about 25 wt % of particles having aparticle size less than 100 μm.

32. The method of claim 27, wherein the particle size distribution includes about 50 wt % of particles having a particle size between about 250 μm, and about 150 μm, about 25 wt % of particles having a particle size between about 150 μm and about 100 μm, and about 25 wt % of particles having a particle size less than about 100 μm.

33. The method of claim 25, wherein the particulate bone is particulate cortical bone, particulate cancellous bone or mixtures or combinations thereof.

34. The method of claim 33, wherein the bone is selected from the group consisting of autograft bone, allograft bone xenograft bone and mixtures or combinations thereof.

35. A composition comprising particulate bone having a particle size distribution comprising from about 24.6 wt % to about 36.3 wt % of particles having a particle size between about 350 μm and about 250 μm, from about 22 wt % to about 25 wt % of particles having a particle size betweeen 250 μm and about 150 μm, and from about 36.7 wt % to about 46.7 wt % of particles having a particle size less than 150 μm, where the particulate bone is non-chemically extracted and non-demineralized and prepared from bone having an initial temperature between about 18° C. and about 20° C. and groung in mill under conditions so that the bone is not heated above a critical temperature of less than or equal to 40° C., and where said composition has improved osteoinductive activity and regeneration of the bone defects as compared as compared to demineralized particulate bone.

36. The composition of claim 35, wherein the particulate bone is particulate cortical bone, particulate cancellous bone or mixtures or combinations thereof.

37. The composition of claim 35, wherein the bone is selected from the group consisting of autograft bone, xenograft bone and mixtures or combinations thereof.

* * * * *